(12) United States Patent
Vertesy et al.

(10) Patent No.: US 6,756,402 B2
(45) Date of Patent: Jun. 29, 2004

(54) CYCLIPOSTINS, PROCESS FOR THEIR PREPARATION AND USE THEREOF

(75) Inventors: Laszlo Vertesy, Eppstein-Vockenhausen (DE); Klaus Ehrlich, Rüsselsheim (DE); Michael Kurz, Hofheim (DE); Joachim Wink, Rödermark (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/886,044

(22) Filed: Jun. 22, 2001

(65) Prior Publication Data

US 2002/0058645 A1 May 16, 2002

Related U.S. Application Data

(63) Continuation-in-part of application No. 09/847,277, filed on May 3, 2001.

(30) Foreign Application Priority Data

May 4, 2000 (DE) .......................................... 100 21 731
Apr. 25, 2001 (EP) .................................. PCT/EP01/04652

(51) Int. Cl.$^7$ .................... A61K 31/335; C07D 321/00; C07F 9/02
(52) U.S. Cl. .................... 514/450; 549/351; 558/83; 558/85; 558/86
(58) Field of Search .................... 514/450; 549/351; 558/83, 85, 86

(56) References Cited

PUBLICATIONS

Izawa, T., et al., "Antibiotic NK901093A, Its Manufacture with Streptomyces, and Insecticides and Acaricides Containing NK901093A", Chemical Abstracts, vol. 121, No. 7, (1994).

Kurokawa, T., et al., "Fermentative Preparation of Antibiotic NK901093 as Insectide and Miticide", Chemical Abstracts, vol. 118, No. 1, (1993).

T. Kurokawa, Cyclophostin, Acetylcholinesterase Inhibitor From *Strepomyces Iavendulae*, *The Journal of Antibiotics*, vol. 46, No. 8, (1993), pps. 1315–1318.

R. Neumann et al., Insecticidal Organophosphated: Nature Made Them First, *Experienta*, vol. 43, (1987), pps. 1235–1237.

*Primary Examiner*—Deborah C. Lambkin
(74) *Attorney, Agent, or Firm*—Finnegan, Henderson, Farabow, Garrett & Dunner L.L.P.

(57) ABSTRACT

The invention relates to compounds of formula I

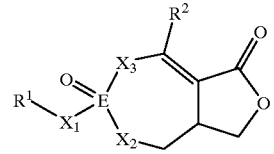

I in which $R^1$, $R^2$, E, $X_1$, $X_2$, and $X_3$ have the meaning as described in the specification and claims, obtained by culturing Streptomyces species HAG 004107 (DSM 13381), and their physiologically tolerable salts and chemical equivalents. The invention furthermore relates to a process for the preparation of the cyclipostins, the microorganism HAG 004107 (DSM 13381), the use of the cyclipostins and their physiologically tolerable salts and chemical equivalents as pharmaceuticals, in particular as inhibitors of lipases, and pharmaceutical preparations which contain cyclipostin or a physiologically tolerable salt or equivalent thereof.

13 Claims, No Drawings

CYCLIPOSTINS, PROCESS FOR THEIR PREPARATION AND USE THEREOF

This is a continuation-in-part of U.S. application Ser. No. 09/847,277, filed May 3, 2001, which claims priority of German Application No. 10021731.1-43, filed on May 4, 2000, the disclosures of which are incorporated by reference. This application also claims the benefit of priority under 35 U.S.C. §119 to PCT application PCT/EP 01/04652, filed on Apr. 25, 2001, the disclosure of which is incorporated by reference.

The invention relates to novel compounds, called cyclipostins, obtainable by culturing Streptomyces species HAG 004107 (DSM 13381), and their physiologically tolerable salts and chemical equivalents. The invention furthermore relates to a process for the preparation of the cyclipostins, the microorganism HAG 004107 (DSM 13381), the use of the cyclipostins and their physiologically tolerable salts and chemical equivalents as pharmaceuticals, in particular as inhibitors of lipases, and pharmaceutical preparations which contain cyclipostin or a physiologically tolerable salt or equivalent thereof.

A disease which can be treated particularly advantageously with lipase inhibitors is the sugar disease diabetes mellitus. Diabetes mellitus is a condition which is characterized by increased blood sugar concentrations on account of chronic metabolic disorders. The metabolic disorders are based on an insulin deficiency or reduced insulin action. Reduced insulin action leads to defective utilization by the body cells of the glucose absorbed in the blood. On account of this and because of neogenesis of glucose from proteins (gluconeogenesis), there is a rise in the blood glucose level. Moreover, in the case of decreased insulin action in the fatty tissue, the insulin-antagonistic hormones, such as glucagon, lead to increased lipolysis and thus to raised fatty acid concentrations in the blood. Ketoacidosis occurs, i.e., the increased formation of ketone bodies (acetic acid, β-hydroxybutyric acid, acetone). Under acute conditions, the extent of the biochemical dysregulation is life-threatening and, if untreated, leads to diabetic coma and finally to rapid death. Diabetes is one of the most frequent chronic metabolic disorders of man and it is estimated that up to more than 3% of the population have a diabetic or prediabetic disposition and are thus may be acutely threatened. There is therefore a great need for agents for the treatment or cure of diabetes mellitus.

Diabetes is treated by insulin administration. In adult-onset diabetes, the so-called noninsulin-dependent (NIDDM) or type II diabetes, sulfonylureas are first administered. The principle of action of the sulfonylureas is via proliferation of the secretion of insulin of the β-cells in the pancreas, thus compensating for the hormone deficiency or the insulin resistance. Upon progression of the condition, however, insulin also has to be employed. The action of insulin can be summarized in the following way. This peptide hormone lowers the concentration of the glucose in the blood and leads to an increase in anabolic processes and simultaneously to an inhibition of catabolic processes:

it increases the glucose transport into the body cells;
it increases the glycogen formation in the liver and in the muscles;
it inhibits lipolysis;
it increases the absorption of fatty acids into the fatty tissue; and
it increases the absorption of amino acids into the body cells and protein synthesis.

One of the strongest effects of insulin is the inhibition of lipolysis. In the case of type II diabetics, this regulation of lipolysis is no longer effective and an increased level of free fatty acids in the blood occurs. Free fatty acids in the blood stimulate gluconeogenesis in the liver and decrease utilization of glucose in the skeletal muscles. Lipolysis (the release of fatty acids by the so-called hormone-sensitive lipase (HSL), which is found in the fat cells and is inhibited by insulin by a phosphorylation cascade) is controlled. Inhibitors of HSL would therefore be desirable which stimulate the action of insulin and are able to lower the blood lipid level. Such agents are suitable for the treatment of type II diabetics to control the lipid metabolism, but applications would also be possible in other storage disorders. For these reasons, novel inhibitors of HSL and other lipases are urgently needed and therefore sought.

Surprisingly the microorganism strain Streptomyces species HAG 004107, DSM 13381, is able to form highly active novel lipase inhibitors which inhibit the hormone-sensitive lipase even at very low concentrations. The novel natural compounds are organophosphates which consist of a double ring system (bicycle) and a substituted carbon chain. The compounds specifically inhibit the lipases. The ring structure was described for the first time, with a methyl group instead of a carbon chain, as an acetylcholine esterase inhibitor, CGA 134 736, by R. Neumann & H. H. Peter in *Experientia*, 43:1235–1237 (1987). The same compound was designated as "cyclophostin," by T. Kurokawa et al. in *J. Antibiotics*, 46:1315–1318 (1993). This structurally related compound has no selective lipase-inhibiting properties. The previously known substances have disadvantages which are manifested in an unsatisfactory level of action, high toxicity and/or undesirable side effects.

The present invention therefore relates to compounds of formula I

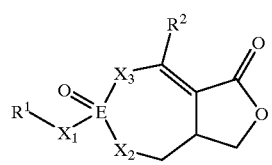

wherein
$R^1$ is
(a) a carbon chain having 2 to 30 carbon atoms, which can be straight-chain, branched, saturated or unsaturated, carbo- or heterocyclic, and wherein the carbon chain is optionally mono- or disubstituted by a radical selected from:
(a)(1) —OH,
(a)(2) =O,
(a)(3) —O—$C_1$-$C_6$-alkyl, in which alkyl is linear or branched,
(a)(4) —O—$C_2$-$C_6$-alkenyl, in which alkenyl is linear or branched,
(a)(5) —$C_1$-$C_6$-alkyl, in which alkyl is linear or branched,
(a)(6) —aryl,
(a)(7) —$C_1$-$C_6$-alkylbenzene,
(a)(8) —diphenyl,
(a)(9) —NH—$C_1$-$C_6$-alkyl, in which alkyl is linear or branched,
(a)(10) —NH—$C_2$-$C_6$-alkenyl, in which alkenyl is linear or branched, (a)(11) —NH₂, (a)(12) =S, (a)(13) —S—C₁–C₆-alkyl, in which alkyl is linear or branched, (a)(14) —S—C₂–C₆-alkenyl, in which alkenyl is linear or branched, and (a)(15) halogen, wherein the substituents (a)(1) to (a)(15) can also be additionally substituted, or (b)-[-aryl-(CH₂)ₙ]ₘ, wherein [-aryl-(CH₂)ₙ]ₘ is unsubstituted, or mono- or disubstituted by a radical as described in (a)(1) to (a)(15), and n and m independently of one another are integers zero, 1, 2, or 3;

R² is

C₁–C₆-alkyl, in which alkyl is unsubstituted or mono- or disubstituted by a radical as described in (a)(1) to (a)(15), C₂–C₆-alkenyl, in which alkenyl is unsubstituted or mono- or disubstituted by a radical as described in (a)(1) to (a)(15), or C₂–C₆-alkynyl, in which alkynyl is unsubstituted or mono- or disubstituted by a radical as described in (a)(1) to (a)(15), E is a phosphorus (P) or sulfur (S) atom; and X₁, X₂ and X₃, independently of one another, are selected from

—O—,

—NH—,

—N=,

—S—,

—CH₂—, and

—CHR²—.

in all their stereochemical forms and mixtures of these forms in any ratio, and their physiologically tolerable salts and chemical equivalents.

R¹ preferably has a chain length of 6 to 24 carbon atoms, very preferably of 10 to 18 carbon atoms. The chain can be saturated, e.g., -alkyl, in which alkyl can be linear or branched, or unsaturated, e.g., -alkenyl or -alkynyl, in which alkenyl or alkynyl is linear or branched. R₁ can be unsubstituted, or identically or differently mono- or disubstituted by groups (a)(1) to (a)(15), as described above. Substitution on the carbon atoms 8' to 16' is preferred and on the positions 10' to 14' is particularly preferred. The substituents (a)(1) to (a)(15) can also be additionally substituted by one or more groups selected from: alcohol, aldehyde, acetal, ketal, ether, carboxyl, ester, amino, nitrile, nitro, oxime, oxime ether, and halogen.

A carbocyclic carbon chain having 2 to 30 carbon atoms is a chain consisting of 2 to 30 carbon atoms with one or more, preferably with one, with two, or with three ring systems, which preferably in each case consists of 4, 5, 6 or 7 carbon atoms. The rings can be mono-, di- or tricyclic, preferably monocyclic, and may be positioned at the beginning, in the center, and/or at the end of the carbon chain. The carbocycles can be aliphatic or aromatic in nature. Some examples are substituted diphenyls or alkylbenzenes.

A heterocyclic carbon chain having 2 to 30 carbon atoms is a chain consisting of 2 to 30 carbon atoms having one or more, preferably having one to three, ring systems in which at least one carbon atom is replaced by a heteroatom, such as O, S, or N. These rings can be mono-, di-, or tricyclic, preferably monocyclic, and can be positioned at the beginning, in the center, and/or at the end of the carbon chain. They can preferably be 4-, 5-, 6- or 7-membered rings, which are aliphatic or aromatic in nature. Some examples are alkyl piperidines, which may be substituted or unsubstituted.

Aryl is an aromatic ring or ring system having 6 to 14, preferably 6 to 10, carbon atoms, such as optionally substituted alkylphenol or alkylnaphthol. Halogen is chloride, bromide, fluoride, or pseudohalides, such as cyanide (nitrile).

—C1–C6-alkyl is a straight-chain or branched alkyl having 1, 2, 3, 4, 5, or 6 carbon atoms, such as methyl, ethyl, i-propyl, tert-butyl, and hexyl.

—C2–C6-alkenyl is a straight-chain or branched alkenyl having 2, 3, 4, 5, or 6 carbon atoms, such as allyl, crotyl, and pentenyl.

—C2–C6-alkynyl is a straight-chain or branched alkynyl having 2, 3, 4, 5, or 6 carbon atoms, such as propynyl, butynyl, and pentynyl.

In one embodiment of the present invention, R¹ may be any of:

—(CH₂)₁₅CH₃,

—(CH₂)₁₃CH(CH₃)₂,

—(CH₂)₁₁CH(OH)(CH₂)₃CH₃,

—(CH₂)₁₁CH(OH)CH₂CH(CH₃)₂,

—(CH₂)₁₂CH(OH)(CH₂)₂CH₃,

—(CH₂)₁₃CH(OH)CH₂CH₃,

—(CH₂)₁₄CH(OH)CH₃,

—(CH₂)₁₅CH₂(OH),

—(CH₂)₁₆CH₃, or

—(CH₂)₁₃C=OCH₂CH₃

—(CH₂)₁₂C=OCH₂CH₂CH₃

—(CH₂)₁₁C=OCH₂CH₂CH₂CH₃

—(CH₂)₁₃CH₃

—(CH₂)₁₁CH(CH₃)₂

—(CH₂)₁₄CH₃ or

—(CH₂)₁₂CH(CH₃)₂.

In another embodiment, R² is C₁–C₆-alkyl, methyl, ethyl, or propyl.

Some of the compounds of the invention are indicated below:

Cyclipostin A of formula II:

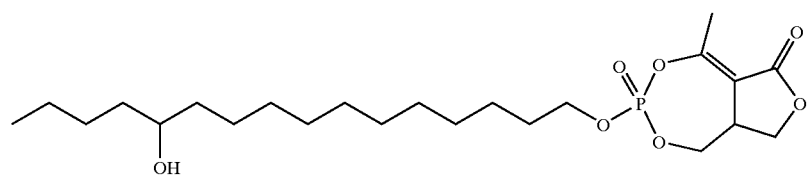

II

-continued
Cyclipostin A 2 of formula II A:
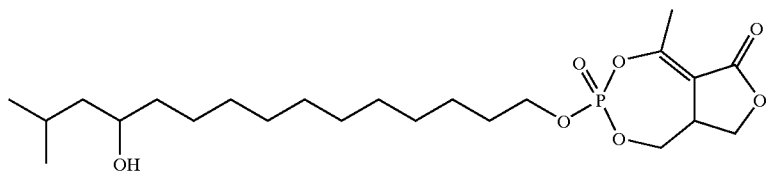
IIA
Cyclipostin B of formula III:
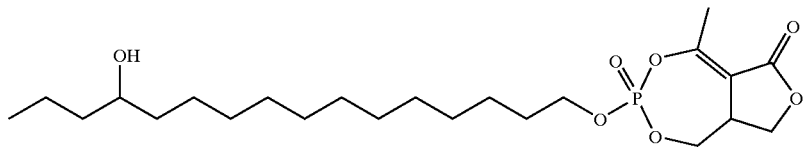
III
Cyclipostin C of formula IV:
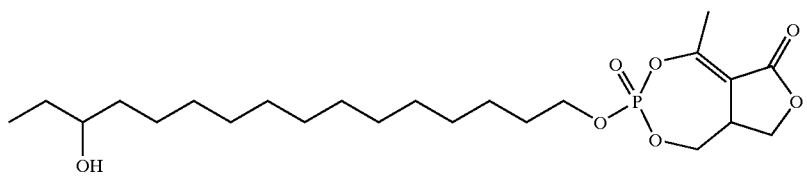
IV
Cyclipostin D of formula V:
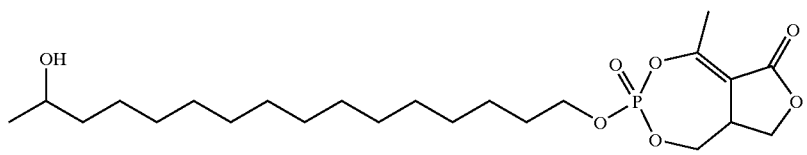
V
Cyclipostin E of formula VI:
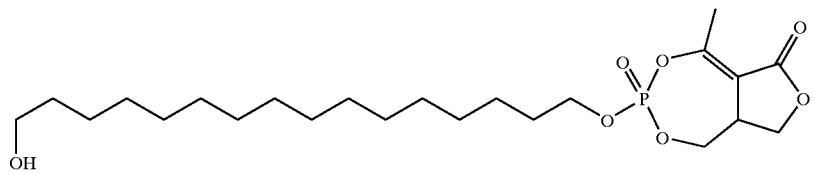
VI
Cyclipostin F of formula VII:
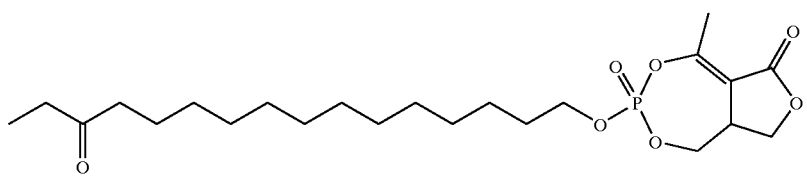
VII
Cyclipostin G of formula VIII:
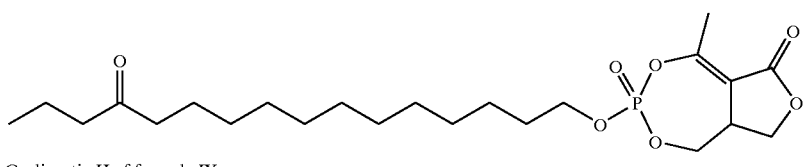
VIII
Cyclipostin H of formula IX:
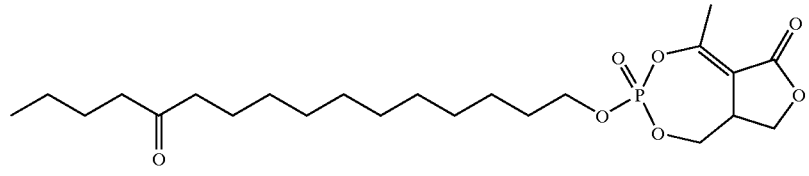
IX -continued
Cyclipostin N of formula X:
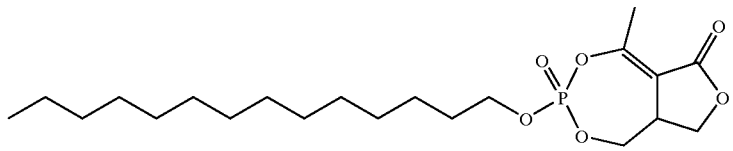
X
Cyclipostin P of formula XI:
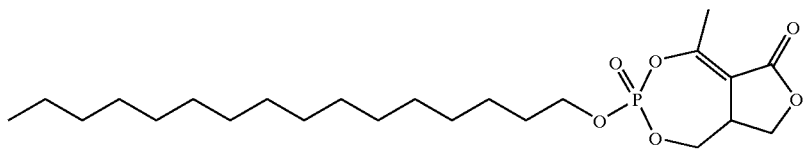
XI
Cyclipostin P 2 of formula XI A:
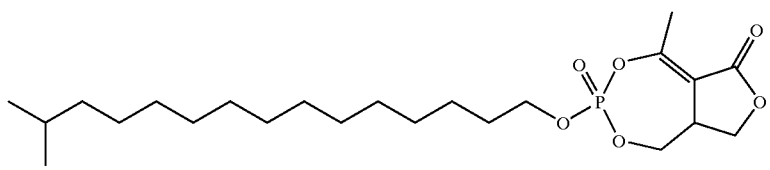
XIA
Cyclipostin Q of formula XII:
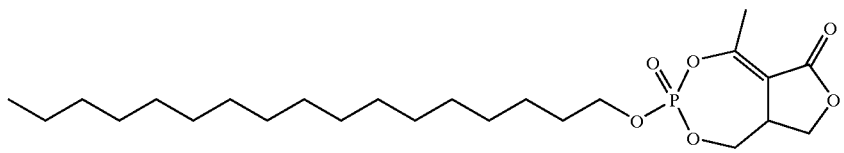
XII
Cyclipostin R of formula XIII:
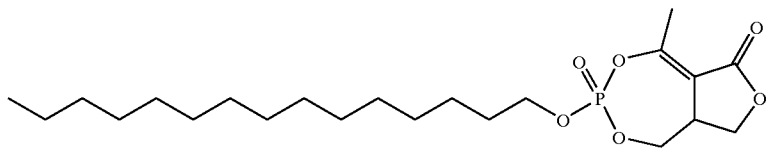
XIII
Cyclipostin R2 of formula XIIIA:
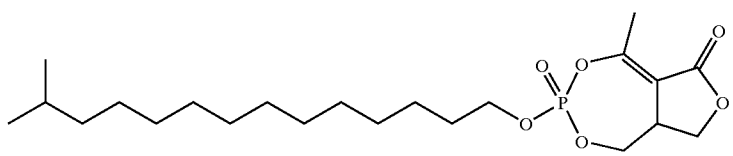
XIIIA
Cyclipostin S of formula XIV:
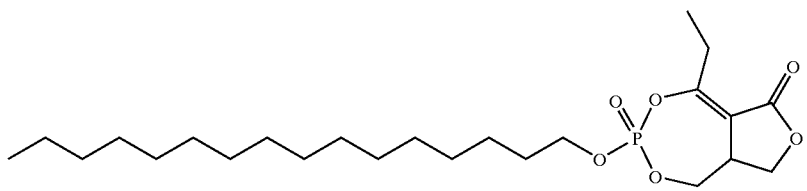
XIV
Cyclipostin T of formula XV:
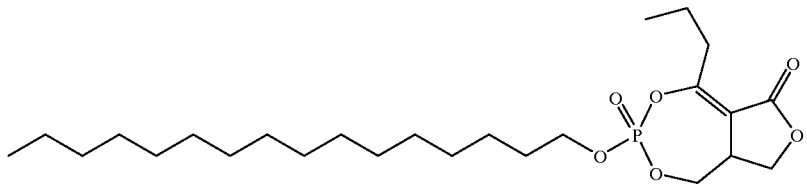
XV Cyclipostin T2 of formula XV A:

XVA

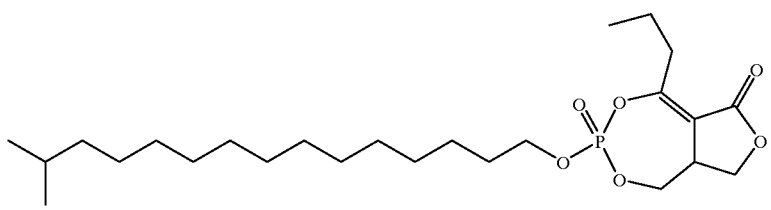

all their stereochemical forms and mixtures of these forms in any ratio, and their physiologically tolerable salts and chemical equivalents.

The manner of numbering of the carbon atom positions for the NMR spectra in the cyclopostin formulae is as follows:

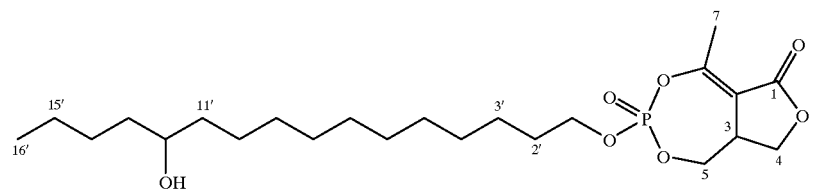

The ring system alone contains two asymmetrically substituted atoms, the carbon atom 3 (C3) and the phosphorus atom. Both atoms can be present in an R or S configuration. It has surprisingly been found that the strain Streptomyces species HAG 004107, DSM 13381, is able in each case to form a number of stereoisomers of the compounds of formula I, that is the strain synthesizes compounds in which the atoms C3 and P, independently of one another, can assume an R or S configuration. Isomers having on C3 in an R configuration and on phosphorus in an S configuration occur in increased amount in cultures of the Streptomyces species HAG 004107, DSM 13381. See formula IA:

IA

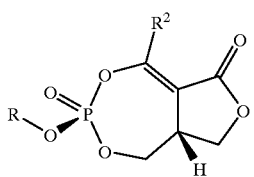

In addition, however, cyclipostins having other configurations, such as (R,R), (S,S) or (S,R) are also formed, which surprisingly also have considerable lipase-inhibitory actions. These cyclipostins are also encompassed within the present invention.

The compound of formula I, or of a physiologically tolerable salt or chemical equivalent thereof, may be prepared by fermenting the microorganism Streptomyces species HAG 004107, DSM 13381, or one of its variants or mutants under suitable conditions in a culture medium until at least one compound of formula I accumulates in the culture medium isolating said compound from the culture medium, and optionally converting said compound into chemical equivalents and physiologically tolerable salts.

The cyclipostins according to the invention can be produced by Actinomycetales species, preferably by Streptomyces species HAG 004107, DSM 13381. Streptomyces species HAG 004107, DSM 13381 has an ivory-colored mycelium (RAL 1014) and is characterized by the conidiophora characteristic of Streptomycetes.

An isolate was deposited in the Deutsche Sammlung von Mikroorganismen and Zellkulturen GmbH, Mascheroder Weg 1B, D 38124 Braunschweig, Germany, according to the rules of the Budapest Convention, on Mar. 16, 2000, under the following number Streptomyces species HAG 004107, DSM 13381.

Instead of, or in addition to, the strain Streptomyces species HAG 004107, DSM 13381, it is also possible to employ its mutants and variants which synthesize one or more compounds of the cyclipostins according to the invention. Such mutants can be produced in a manner known per se by physical means, for example irradiation, such as with ultraviolet or X-rays, or by chemical mutagens, such as ethyl methanesulfonate (EMS), 2-hydroxy-4-methoxy-benzophenone (MOB), or N-methyl-N'-nitro-N-nitrosoguanidine (MNNG).

The invention thus relates to a process for the preparation of the compound of formula I or a physiologically tolerable salt thereof, which comprises fermenting the microorganism Streptomyces species HAG 004107, DSM 13381, or one of its variants or mutants under suitable conditions in a culture medium until one or more compounds of formula I accumulate in the culture medium, isolating them from the culture medium, and optionally converting them into chemical equivalents and physiologically tolerable salts.

Preferably, the strain Streptomyces species HAG 004107, DSM 13381, its mutants and/or variants, is fermented in a nutrient solution (also called a culture medium) with a carbon and nitrogen source and the customary inorganic salts until at least one novel cyclipostin accumulates in the culture medium, then the cyclopostin(s) are isolated from the culture medium, and optionally separated into the individual active components.

The fermentation is preferably carried out under aerobic conditions; it proceeds particularly well at a temperature between about 18 and 35° C. and at a pH between about 6 and 8.

The process according to the invention can be employed for fermentation on the laboratory scale (milliliter to liter range) and for the industrial scale (cubic meter scale). All percentages relate, if not stated otherwise, to the weight. Mixing ratios in the case of liquids relate to the volume, if no other details are given.

Suitable carbon sources for aerobic fermentation by methods according to the invention are assimilable carbohydrates and sugar alcohols, such as glucose, lactose, sucrose, or D-mannitol, and carbohydrate-containing natural products, such as oat flakes, soybean flour, and malt extract. Possible nitrogen-containing nutrients are: amino acids, peptides, and proteins, and their degradation products, such as peptones or tryptones, furthermore meat extracts, yeast extracts, ground seeds, for example of corn, wheat, beans, soya beans, or the cotton plant, distillation residues of alcohol production, meat meals, or yeast extracts, but also ammonium salts and nitrates. Inorganic salts which the nutrient solution can contain are, for example, chlorides, carbonates, sulfates, or phosphates of the alkali metals or alkaline earth metals, iron, zinc, cobalt, and manganese.

The formation of the cyclipostins of the formulae II to XV A according to the invention proceed well in a culture medium which contains approximately 0.1 to 5%, preferably 0.3 to 3%, of oat flakes and trace elements. The details in percent are in each case based on the weight of the entire culture medium.

The preferred formation of the cyclipostins of the formulae VIII to XV A can be particularly readily carried out in nutrient solutions which contain approximately 0.1 to 5%, preferably 0.3 to 2%, of glycerol, and 0.2 to 5%, preferably 0.5 to 3%, of soya bean meal, and 0.05 to 1.0 g/L, preferably 0.1 to 1.0 g/L, of sodium chloride.

In culture medium, Streptomyces species HAG 004107, DSM 13381, forms a mixture of cyclipostins. Depending on the composition of the culture medium, the quantitative amount of one or more of the cyclipostins according to the invention can vary. Moreover, it is possible by means of the media composition to control the synthesis of individual cyclipostins such that one or alternatively more of the cyclipostins is not prepared at all or is prepared in an amount below the detection limit of the microorganism.

The culture preferably contains a detectable cyclipostin. The cyclipostins A or P or P 2 are specific embodiments of the present invention.

In addition to the cyclipostins A to T2 (compounds of formulae II to XV A), further related compounds are formed in the culture medium of Streptomyces species HAG 004107, DSM 13381, which differ from the compounds shown in the formulae II to XV A by having modified radicals $R^1$ and $R^2$. In smaller amounts, cyclipostins have been detected which have a truncated or further branched radical $R^1$. Oxidation (hydroxylation) products of these secondary components are also detectable in cultures of Streptomyces HAG 004107, DSM 13381.

The culturing of the microorganism is carried out aerobically, i.e., by submerging with shaking or stirring in shake flasks or fermenters, if appropriate with the introduction of further air or oxygen. It can be carried out in a temperature range from approximately 18 to 35° C., preferably at approximately 25 to 32° C., in particular at approximately 26 to 30° C. The pH range should be between about 6 and 8, preferably between about 6.5 and 7.8. The microorganism is cultured under these conditions, in general, for a period of 24 to 300 hours, preferably 30 to 90 hours.

Advantageously, culturing is carried out in a number of stages, i.e., first one or more precultures is/are prepared in a liquid culture medium, which is then inoculated into the actual production medium, the main culture, for example, in the volume ratio 1:10. The preculture is obtained, for example, by inoculating a mycelium into a nutrient solution and allowing it to grow for approximately 36 to 120 hours, preferably 48 to 96 hours. The mycelium can be obtained, for example, by allowing the strain to grow for approximately 3 to 40 days, preferably 4 to 10 days, on a solid or liquid nutrient medium, for example malt/yeast/agar or oat flakes/agar.

The course of fermentation can be monitored by means of the pH of the cultures or of the mycelium volume, and by chromatographic methods, such as thin-layer chromatography or high-pressure liquid chromatography (HPLC), or by testing the biological activity. The cyclipostins according to the invention are present in the mycelium and to a smaller part also in the culture filtrate. The isolation process described below serves for the purification of the cyclipostins according to the invention, preferably for the purification of the cyclipostins A and P.

The isolation and/or purification of the cyclipostins according to the invention from the culture medium is carried out according to known methods, taking into account the chemical, physical, and biological properties of the natural substances. For the testing of the cyclipostin concentration in the culture medium or in the individual isolation stages, thin-layer chromatography, for example, on silica gel using methylene chloride/ethyl acetate or chloroform/methanol mixtures (e.g., in the quantitative ratio 98:1) as eluent, or HPLC, can be used. The detection in the case of thin-layer chromatographic separation can be carried out, for example, by means of color reagents such as molybdatophosphoric acid or $I_2$ vapor, the amount of the substance formed expediently being compared with a calibration solution.

For the isolation of the cyclipostins according to the invention, the mycelium is first separated off from the culture medium according to the customary processes and the cyclipostins are then extracted from the cell mass using an organic solvent which is optionally miscible with water. The organic solvent phase contains the cyclipostins according to the invention; they are optionally concentrated -in vacuo and further purified as described below.

The culture filtrate is optionally combined with the concentrate of the mycelium extract and extracted with a suitable water-immiscible organic solvent, for example with n-butanol or ethyl acetate. The organic phase is subsequently separated off and optionally concentrated in vacuo and dissolved in 1/30 of the original volume of water/methanol.

The further purification of one or more of the cyclipostins according to the invention is carried out by chromatography on suitable materials, preferably, for example, on molecular sieves, on normal-phase supports, such as silica gel, alumina, on ion exchangers or on adsorber resins or on reverse phases (reversed phase, RP). The cyclipostins are separated with the aid of these chromatographic processes. The chromatography of the cyclipostins is carried out using organic solvents or using mixtures of aqueous and organic solutions.

Mixtures of aqueous or organic solutions are understood as meaning any water-miscible organic solvents, preferably methanol, propanol and acetonitrile, in a concentration of 10 to 100% of solvent, preferably 60 to 90% of solvent, or, alternatively, any buffered aqueous solutions which are miscible with organic solvents. The buffers to be used are the same as indicated above.

The separation of the cyclipostins on the basis of their differing polarity is carried out with the aid of reversed phase chromatography, for example on an MCI® (adsorber resin from Mitsubishi, Japan) or Amberlite XAD® (Toso Haas), on further hydrophobic materials, such as on RP-8 or RP-18 phases. Moreover, the separation can be carried out with the aid of normal-phase chromatography, for example on silica gel, alumina and the like.

The chromatography of the cyclipostins is carried out using buffered or acidified aqueous solutions or mixtures of aqueous solutions with alcohols or other, water-miscible organic solvents. The organic solvent used is preferably propanol or acetonitrile.

Buffered or acidified aqueous solutions are understood as meaning, for example, water, phosphate buffer, ammonium acetate, or citrate buffer in a concentration of 1 mM to 0.5 M, and formic acid, acetic acid, trifluoroacetic acid, or all commercially available acids known to the person skilled in the art, preferably in a concentration of 0.01 to 3%, in particular 0.1%.

Chromatography is carried out using a gradient which begins with 100% aqueous buffer and ends with 100% solvent; preferably a linear gradient of 50 to 100% 2-propanol or acetonitrile is run.

Alternatively, gel chromatography or chromatography on hydrophobic phases can also be carried out.

Gel chromatography is carried out on polyacrylamide or mixed polymer gels, such as BIOGEL-P 2® (Biorad), Fractogel TSK HW 40® (Merck, Germany or Toso Haas, USA) or on SEPHADEX® (Pharmacia, Uppsala, Sweden).

The chromatographies used may be performed in any sequence.

Another very effective purification step for cyclipostins is crystallization. The cyclipostins are crystallized from solutions in organic solvents and from mixtures of water with organic solvents. The crystallization is carried out in a manner known per se, for example by concentrating or cooling saturated cyclipostin solutions.

The cyclipostins according to the invention are stable in the solid or liquid state and in solutions in the pH range between about 4 and 8, in particular about 5 and 7, and can thus be incorporated into customary pharmaceutical preparations.

The invention further comprises obvious chemical equivalents of the compounds of formula I which have a slight chemical difference, i.e., have the same activity or can be converted into the compound according to the invention under mild conditions. The equivalents mentioned include, for example, esters and ethers, and oxidation, reduction and hydrogenation products of the compounds according to the invention.

Esters, and ether derivatives, oxidation, hydrogenation and reduction products can be prepared according to processes described in the literature, e.g., in "Advanced Organic Synthesis", $4^{th}$ Edition, J. March, John Wiley & Sons (1992).

The present invention includes all stereoisomeric forms of the compounds of the formulae I to XV A. Asymmetric centers contained in the compounds of the formulae I to XV A can all independently of one another have the S configuration or the R configuration. The invention includes all possible enantiomers and diastereomers, as well as mixtures of two or more stereoisomeric forms, for example mixtures of enantiomers and/or diastereomer, in all ratios. The invention thus relates to enantiomers in enantiomerically pure form, both as rotatory and as dextrorotatory antipodes, R and S configurations, in the form of racemates and in the form of mixtures of the two enantiomers in all ratios. In the presence of cis/trans isomerism, the invention relates both to the cis form and the trans from and mixtures of these forms in all ratios.

On account of their valuable pharmacological properties, the compounds according to the invention are suitable for use as pharmaceuticals in human and/or veterinary medicine. They inhibit lipases and have properties favorable for the treatment of metabolic disorders which have their cause in the disturbance of the lipid metabolism. The compounds of formula I according to the invention have a surprising inhibitory action on the hormone-sensitive lipase, HSL, an allosteric enzyme in adipocytes, which is inhibited by insulin and is responsible for the breakdown of fats in fat cells and thus for the transfer of fat constituents into the blood stream. Inhibition of this enzyme thus corresponds to an insulin-like action of the compounds according to the invention, which finally leads to a decrease in free fatty acids in the blood and in blood sugar. They can thus be employed in dysfunctions of the metabolism such as in noninsulin-dependent diabetes mellitus, in the diabetic syndrome, and in direct damage to the pancreas.

The invention thus relates to pharmaceutical preparations which contain one or more of the cyclipostins according to the invention and/or chemical equivalents thereof. Use as a mixture with suitable excipients or carrier material is preferred. Carrier materials which can be employed in humans are all pharmacologically tolerable carrier materials and/or excipients.

The invention further relates to a process for the preparation of a pharmaceutical according to the invention, which comprises bringing at least one of the compounds according to the invention into a suitable administration form using a pharmaceutically suitable and physiologically tolerable carrier and, if appropriate, further suitable active compounds, additives or excipients.

The pharmaceuticals according to the invention are in general administered orally, locally, or parenterally, but rectal administration is in principle also possible. Suitable solid or liquid pharmaceutical preparation forms are, for example, granules, powders, tablets, coated tablets, (micro) capsules, suppositories, syrups, emulsions, suspensions, aerosols, drops, or injectable solutions in ampule form, and preparations having protracted release of active compound, in whose preparation vehicles and additives and/or excipients such as disintegrants, coating agents, swelling agents, glidants or lubricants, flavorings, sweeteners, or solubilizers are customarily used. Frequently used vehicles or excipients which may be mentioned are, for example, magnesium carbonate, titanium dioxide, lactose, mannitol and other sugars, talc, lactoprotein, gelatin, starch, vitamins, cellulose and its derivatives, animal or vegetable oils, polyethylene glycols, and solvents, such as sterile water, alcohols, glycerol and polyhydric alcohols.

If appropriate, the dose units can be microencapsulated for oral administration in order to delay release or to extend it over a longer period, such as by coating or embedding the active compound in particle form in suitable polymers, waxes or the like.

Preferably, the pharmaceutical preparations are prepared and administered in dose units, each unit containing as active constituent a specific dose of one or more compounds of the cyclipostins according to the invention and/or chemical derivatives thereof. In the case of solid dose units such as tablets, capsules and suppositories, this dose can be up to approximately 200 mg, but preferably approximately 0.1 to 100 mg, and in the case of injection solutions in ampule form up to approximately 200 mg, but preferably approximately 0.1 to 100 mg, per day.

The daily dose to be administered is dependent on the body weight, age, sex, and condition of the mammal. Under certain circumstances, however, higher or lower daily doses may also be appropriate. The administration of the daily dose can be carried out either by single administration in the form of an individual dose unit or else in a number of smaller dose units or by repeated administration of subdivided doses at-specific intervals. The invention also relates to pharmaceutical preparations which contain one or more of the cyclipostins according to the invention and/or chemical derivatives thereof. Use as a mixture with suitable excipients or carrier material is preferred. In the case of humans, the carrier material used can be all pharmacologically tolerable carrier materials and/or excipients.

The action of compounds of formula I according to the invention was tested on the following enzyme test system, and is presented in Example 21.

Enzyme Preparation

Preparation of the Partially Purified HSL

Isolated rat lipocytes were obtained from epididymal fatty tissue of nontreated male rats (Wistar, 220–250 g) by collagenase treatment according to published procedures (e.g., S. Nilsson et al., *Anal. Biochem.* 158:399–407 (1986); G. Fredrikson et al., *J. Biol. Chem.* 256, 6311–6320 (1981); H. Tornquist et al., *J. Biol. Chem.* 251:813–819 (1976)). The lipocytes from 10 rats were washed three times by flotation with 50 ml of homogenization buffer in each case (25 ml TRIS/HCl, pH 7.4, 0.25 M sucrose, 1 mM EDTA, 1 mM DTT, 10 $\mu$g/ml of leupeptin, 10 $\mu$g/ml of antipain, 20 $\mu$g/ml of pepstatin) and finally taken up in 10 ml of homogenization buffer. The lipocytes were homogenized in a Teflon-in-glass homogenizer (Braun-Melsungen) by means of 10 strokes at 1500 rpm and 15° C. The homogenisate was centrifuged (Sorvall SM24 tubes, 5000 rpm, 10 min, 4° C.). The lower layer between the overlying fatty layer and the pellet was removed and the centrifugation was repeated. The lower layer resulting from this was centrifuged again (Sorvall SM24 tubes, 20000 rpm, 45 min, 4° C.). The lower layer was removed and treated with 1 g of heparin-sepharose (Pharmacia-Biotech, CL-6B, washed 5× with 25 mM Tris/HCl, pH 7.4, 150 mM NaCl). After incubation for 60 min at 4° C. (shaken at intervals of 15 min), the batch was centrifuged (Sorvall SM24 tubes, 3000 rpm, 10 min, 4° C.). The supernatant was brought to pH 5.2 by addition of acetic acid and incubated at 4° C. for 30 min. The precipitates were collected by centrifugation (Sorvall SS34, 12000 rpm, 10 min, 4° C.) and suspended in 2.5 ml of 20 mM Tris/HCl, pH 7.0, 1 mM EDTA, 65 mM NaCl, 13% of sucrose, 1 mM DTT, 10 $\mu$g/ml of leupeptin/pepstatin/antipain. The suspension was dialyzed overnight at 4° C. against 25 mM Tris/HCl, pH 7.4, 50% of glycerol, 1 mM DTT, 10 $\mu$g/ml of leupeptin, pepstatin, and antipain, and then applied to a hydroxylapetite column (0.1 g per 1 ml of suspension, equilibrated with 10 mM potassium phosphate, pH 7.0, 30% of glycerol, 1 mM DTT). The column was washed with four volumes of equilibration buffer at a flow rate of 20 to 30 ml/h. The HSL was eluted with a volume of equilibration buffer which contained 0.5 M potassium phosphate, then dialyzed (see above), and was concentrated 5 to 10 times by ultrafiltration (Amicon Diaflo PM 10 Filter) at 4° C. The partially purified HSL could be stored at −70° C. for 4 to 6 weeks.

Assay

For the preparation of the substrates, 25–50 $\mu$Ci of [$^3$H] trioleoylglycerol (in toluene), 6.8 $\mu$Mol of unlabeled trioleoylglycerol and 0.6 mg of phospholipid (phosphatidylcholine/phosphatidylinositol 3:1 w/v) were mixed, dried by means of $N_2$ and then taken up in 2 ml of 0.1 M $KP_i$ (pH 7.0) by ultrasonic treatment (Branson 250, microtips, setting 1–2, 2×1 min at a 1 min interval). After addition of 1 ml of $KP_i$ and fresh ultrasonic treatment (4×30 sec on ice at 30 sec intervals), 1 ml of 20% BSA (bovine serum albumin) (in $KP_i$) was added (final concentration of trioleoylglycerol at 1.7 mM). For the reaction, 100 $\mu$l of substrate solution were pipetted into 100 $\mu$l of HSL solution (HSL prepared as above, diluted in 20 mM $KP_i$, pH 7.0, 1 mM EDTA, 1 mM DTT, 0.02% BSA, 20 $\mu$g/ml of pepstatin, 10 $\mu$g/ml of leupeptin) and incubated at 37° C. for 30 min. After addition of 3.25 ml of methanol/chloroform/heptane (10:9:7) and of 1.05 ml 0.1 M $K_2CO_3$, 0.1 M boric acid (pH 10.5), the batch was mixed well and finally centrifuged (800×g, 20 min). After phase separation, one equivalent of the upper phase (1 ml) was removed and the radioactivity was determined by liquid scintillation measurement.

Evaluation

Substances were generally tested in four independent batches. The inhibition of the enzymatic activity of the HSL by a test substance was determined by the comparison with a noninhibited control reaction. The calculation of the $IC_{50}$ value was carried out by means of an inhibitory curve using at least 10 concentrations of the test substance. For the analysis of the data, the GRAPHIT software package, Elsevier-BIOSOFT, was used. In this test, the compounds of the invention showed the following action:

The cyclipostins A, P, P2, and R inhibited the lipolysis in rat adipocytes with $IC_{50}$=~0.2 $\mu$M and they inhibited the human hormone-sensitive lipase (HSL) with trioleoylglycerol as substrate with: $IC_{50}$=~0.01 to 0.5 $\mu$M. With NBD (4-chloro-7-nitrobenzo-2-oxa-1,3-diazole) as a substrate, the HSL from rats was inhibited in concentrations from 4 nM to 10 nM.

The cyclipostins inhibited both the hormone-sensitive lipase (HSL), and the monoacylglycerol lipase of the rat extract at submicromolar concentrations.

The invention is illustrated further in the following examples. Percentages relate to the weight. Mixing ratios in the case of liquids relate to volume, if no other details have been given.

EXAMPLES

Example 1

Preparation of a glycerol culture of Streptomyces species HAG 004107, DSM 13381.

100 ml of nutrient solution (malt extract 2.0%, yeast extract 0.2%, glucose 1.0% $(NH_4)_2HPO_4$ 0.05%, pH 6.0) in a sterile 300 ml Erlenmeyer flask were inoculated with the strain Streptomyces species HAG 004107, DSM 13381, and incubated on a rotating shaker at 28° C. and 180 rpm for 7 days. 1.5 ml of this culture were then diluted with 1.5 ml of 99% strength glycerol and stored at −20° C.

Example 2

Preparation of a preculture in the Erlenmeyer flask of Streptomyces species HAG 004107, DSM 13381.

A sterile 300 ml Erlenmeyer flask containing 100 ml of the following nutrient solution: 15 g/L of glucose, 15 g/L of soybean flour, 5 g/L of cornsteep, 2 g/L of $CaCO_3$ and 5 g/L of NaCl was inoculated with a culture grown on a slant tube (same nutrient solution, but with 2% agar) or with 1 ml of a glycerol culture (see Example 1) and incubated at 180 rpm and 28° C. on a shaker. A 48 to 96-hour-old submerged culture (inoculation amount about 10%) of the same nutrient solution sufficed for the inoculation of 10 and 200 l fermenters.

Example 3

Preparation in Erlenmeyer flasks of a culture of Streptomyces species HAG 004107, DSM 13381.

Sterile 300 ml Erlenmeyer flasks containing 100 ml of the following nutrient solution:

20 g/L of oat flakes for dogs 2.5 ml of trace element solution were inoculated with a 10% inoculation amount of the preculture (Example 2) and incubated at 180 rpm and 28° C. on a shaker. The culture was used after two days for obtaining the cyclipostins or for inoculating fermenters. The trace element solution had the following composition:

3 g/L of $CaCl_2 \times 2H_2O$ 1 g/L of Fe(III) citrate;

0.2 g/L of $MnSO_4 \times H_2O$;

0.1 g/L of $ZnCl_2$;

0.025 g/L of $CUSO_4 \times 5H_2O$, 0.02 g/L of Na tetraborate 0.004 g/L of $CoCl_2 \times 6H_2O$ 0.01 g/L of Na molybdate.

Example 4

Preparation of the cyclipostins of the formulae II to IX.

A 200 L fermenter was operated with 90 liters of nutrient solution under the following conditions:

Nutrient medium:

20 g/L of oat flakes in water;

2.5 ml/l of trace element.

pH 7.8 (before sterilization)

The nutrient solution was heat-sterilized for 30 minutes and, after cooling, 5% of the volume was inoculated with inoculation material obtained according to Example 3.

Trace element solution:

3 g/L of $CaCl_2 \times 2H_2O$ 1 g/L of Fe(III) citrate;

0.2 g/L of $MnSO_4 \times H_2O$;

0.1 g/L of $ZnCl_2$;

0.025 g/L of $CuSO_4 \times 5H_2O$, 0.02 g/L of Na tetraborate 0.004 g/L of $CoCl_2 \times 6H_2O$ 0.01 g/L of Na molybdate.

Process time:

72 hours

Incubation temperature:

28° C.

Stirrer speed:

90 rpm

Aeration:

6 $m^3$ of air per hour.

The fermentation was carried out without addition of antifoam. The production maximum was achieved after about 40 to 76 hours.

Example 5

Preparation of the cyclipostins X to XV A.

A 200 L fermenter was operated under the following conditions with a filling of 100 L:

Nutrient medium:

5 g/L of glucose;

20 g/L of glycerol;

20 g/L of soybean flour;

5 g/L of yeast extract;

3 g/L of NaCl;

2.5 ml/l of trace element solution pH 7.0 (before sterilization)

Process time:

72 hours,

Incubation temperature:

27° C.,

Stirrer speed:

65 rpm,

Aeration:

6 $m^3$ of air per hour.

The fermentation was carried out without addition of agents for suppressing foam formation. The production maximum was achieved after about 48 hours.

Example 6

Isolation of the cyclipostin mixture from the culture solution of Streptomyces species HAG 004107, DSM 13381.

After completion of the fermentation of Streptomyces species HAG 004107, DSM 13381, 100 liters of culture broth from the fermenter, obtained according to Example 4, were filtered with addition of about 2% filter aid (e.g., CELITE®) and the cell mass (10 liters) was extracted with 40 liters of methanol. The active compound-containing, methanolic solution was freed from the mycelium by filtration and concentrated in vacuo. The concentrate was applied to a prepared, 7 liter MCI GEL®, CHP20P column. Elution is carried out using a gradient of water to propan-2-ol. The column flow (20 liters per hour) is collected in fractions (10 liters each) and the fractions containing cyclipostins (19 to 21) were in each case concentrated in vacuo. The fractions were investigated by means of HPLC (see Example 7). Fraction 19 comprised the cyclipostins A to E and their isomers, fraction 20 cyclipostin F and isomers thereof, fraction 21 the inhibitors cyclipostin N, P, P 2, Q, R, S, and T and their isomers.

Example 7

HPLC analysis of the cyclipostins.

High-pressure liquid chromatographic (HPLC) analysis of the cyclipostins was carried out in an HP 1100® unit with YMC Pack Pro C18® columns (AS-303, 250×4.6 mm, S-5 µm, 120 A°). The flow was 1 ml/minute, the column temperature 40° C. A gradient of 0.05% trifluoroacetic acid to acetonitrile was used. 100% acetonitrile was achieved as eluent after 11 minutes and the column was then constantly (isocratically) eluted further with this solvent. Detection was carried out by measuring the ultraviolet absorption at 210 nm. Using this procedure, the cyclipostins had the following retention times:

| | |
|---|---|
| Cyclipostin A | 12.7 minutes, |
| Cyclipostin A 2 | 12.6 minutes, |
| Cyclipostin F | 13.2 minutes, |
| Cyclipostin N | 15.9 minutes, |
| Cyclipostin P | 17.7 minutes, |
| Cyclipostin P 2 | 17.3 minutes, |
| Cyclipostin Q | 18.3 minutes, |
| Cyclipostin R | 16.7 minutes, |

-continued

| | |
|---|---|
| Cyclipostin R2 | 16.4 minutes, |
| Cyclipostin S | 18.5 minutes, |
| Cyclipostin T | 19.1 minutes, and |
| Cyclipostin T2 | 18.7 minutes. |

Example 8

Preparation of pure cyclipostins A and A 2.

Fraction 19, obtained according to Example 6, was concentrated in vacuo and 1 g of the concentrate, dissolved in water/methanol (1:1), was applied to a Nucleoprep 100-5 $C_{18}$ AB® column (21×250 mm). Elution was carried out using a gradient of 50% acetonitrile in 0.01% trifluoroacetic acid to 100% acetonitrile. The flow was 50 ml/minute. The column flow was checked by the measurement of the light absorption at 210 nm and by testing the lipase-inhibiting properties. Fractions of 60 ml each were taken. Cyclipostin A was found in fractions 34 and 35, and cyclipostin A 2 in fractions 41 to 44. These fractions were in each case combined, concentrated in vacuo and separated successively on an SP 250/10 Nucleosil 100-5 C18 HD® column. The gradient chosen was 50% to 66% acetonitrile in 0.01% trifluoroacetic acid and the pH of the solutions was adjusted to 4.0 with a drop of ammoniumhydroxide solution. The fractions which contained pure compounds were in each case combined and freeze-dried. They afforded 5.4 mg of pure cyclipostin A as a waxy substance and 3 mg of cyclipostin A 2 as an oil.

Example 9

Characterization of cyclipostin A.

Appearance: neutral, colorless, waxy substance soluble in oxygen-containing organic solvents, but only slightly soluble in water and petroleum ether.

UV maximum: 228 nm in methanol.

IR bands: 1752 and 1671 $cm^{-1}$.

By high-resolution FAB mass spectrometry using a nitrobenzyl alcohol/LiCl matrix, the following molecular weight was found: 467.2757 amu, corresponding to the empirical formula for cyclipostinin A-Li of $C_{23}H_{41}O_7PLi$. From this, an empirical formula for cyclipostin A of $C_{23}H_{41}O_7P$ resulted, molecular weight: 460. By electron spray mass spectrometry, in the positive ionization mode (ESI, positive) a peak at 461 amu, corresponding to $(M+H)^+$ was found; moreover the characteristic peak at 221 amu, corresponding to $C_7H_{10}O_6P$. In the ESI negative mode, 459 amu $(M-H)^-$, 337 amu $(C_{16}H_{34}O_5P)$ and 219 amu $(C_7H_8O_6P)$ were found. For the determination of the position of the alcohol group, derivatization with N-methyl-N-trimethylsilyltrifluoroacetamide was carried out and the sample was investigated using electron ionization mass spectrometry. The trimethylsilyl derivative resulted:

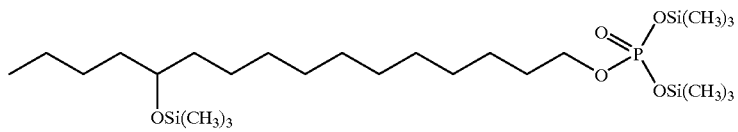

of the mass 554 amu. The position of the silylated hydroxyl group was indicated by the intensive ions at 497 amu (α-cleavage) and 159 amu (α-cleavage). The NMR data for cyclipostin A are shown in Table 1.

TABLE 1

$^1$H and $^{13}$C chemical shifts of cyclipostin A in methanol-$d_4$ at 300 K.

| Position | $^1$H | $^{13}$C |
|---|---|---|
| 1 | — | 171.08 (1.4 Hz)[b] |
| 2 | — | 114.61 (3.4 Hz)[b] |
| 3 | 3.87 | 40.75 |
| 4 | 4.46/3.86 | 66.04 |
| 5 | 4.31/4.25 | 69.39 (6.0 Hz)[b] |
| 6 | — | 161.47 (8.0 Hz)[b] |
| 7 | 2.40 | 17.89 (4.6 Hz)[b] |
| 1' | 4.25 | 71.61 (6.6 Hz)[b] |
| 2' | 1.73 | 31.16 (6.6 Hz)[b] |
| 3' | 1.41 | 26.39 |
| n' | 3.49 | 72.45 |
| n ± 1 | 1.46–1.33 | 38.44, 38.15 |
| 4'–14' (a) | 1.37–1.26 | 30.85–30.58 |
| 15' | 1.34 | 23.84 |
| 16' | 0.91 | 14.43 |

(a) except for n and n ± 1.
[b] the $^{13}$C/$^{31}$P coupling constants are indicated in parentheses.

Example 10

Characterization of cyclipostin B.

Cyclipostin B was isolated as described in Example 8 for cyclipostin A by multiple repetition of the chromatographic steps, and characterized as in Example 9.

Appearance: neutral, colorless, waxy substance soluble in oxygen-containing organic solvents, but only slightly soluble in water and petroleum ether.

UV maximum: 228 nm in methanol.

By electron spray mass spectrometry, in the positive ionization mode (ESI, positive) a peak at 461 amu, corresponding to $(M+H)^+$ was found; moreover the characteristic peak at 221 amu, corresponding to $C_7H_{10}O_6P$. In the ESI negative mode, 459 amu $(M-H)^-$, 337 amu $(C_{16}H_{34}O_5P)$ and 219 amu $(C_7H_8O_6P)$ were found. For the determination of the position of the alcohol group, derivatization was carried out using N-methyl-N-trimethylsilyltrifluoroacetamide and the sample is investigated by electron ionization mass spectrometry. The trimethylsilyl derivative resulted in a mass of 554 amu:

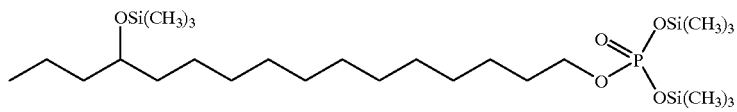

The position of the silylated hydroxyl group was indicated by the intensive ions at 511 amu (α-cleavage) and 145 amu (α-cleavage).

Empirical formula of cyclipostin B: $C_{23}H_{41}O_7P$, molecular weight: 460.

Example 11

Characterization of cyclipostin C.

Cyclipostin C was isolated as described in Example 8 for cyclipostin A by multiple repetition of the chromatographic steps and characterized as in Example 9.

Appearance: neutral, colorless, waxy substance soluble in oxygen-containing organic solvents, but only slightly soluble in water and petroleum ether.

UV maximum: 228 nm in methanol.

By electron spray mass spectrometry, in the positive ionization mode (ESI, positive) a peak at 461 amu, corresponding to (M+H)$^+$ was found; moreover, the characteristic peak at 221 amu was found, corresponding to $C_7H_{10}O_6P$. In the ESI negative mode, 459 amu (M–H)$^-$, 337 amu ($C_{16}H_{34}O_5P$) and 219 amu ($C_7H_8O_6P$) were found. For the determination of the position of the alcohol group, derivatization was carried out using N-methyl-N-trimethylsilyltrifluoroacetamide and the sample was investigated by electron ionization mass spectrometry. The trimethylsilyl derivative resulted in a compound of mass 554 amu:

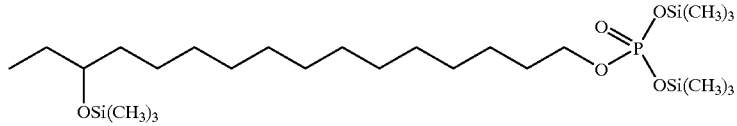

The position of the silylated hydroxyl group was indicated by the intensive ions at 525 amu (α-cleavage) and 131 amu (α-cleavage).

Empirical formula of cyclipostin C: $C_{23}H_{41}O_7P$, molecular weight: 460.

Example 12

Characterization of cyclipostin F.

Fraction 20, obtained according to Example 6, was separated as described in Example 8 and the cyclipostin F was isolated by multiple repetition of the chromatographic steps and characterized as in Example 9.

Reaction time: 13.2 minutes.

Appearance: neutral, colorless, waxy substance soluble in oxygen-containing organic solvents, but only slightly soluble in water and petroleum ether.

UV maximum: 228 nm in methanol.

By electron spray mass spectrometry, in the positive ionization mode (ESI, positive) a peak at 459 amu, corresponding to (M+H)$^+$ was found; moreover the characteristic peak at 221 amu, corresponding to $C_7H_{10}O_6P$. In the ESI negative mode, 457.6 amu (M–H)$^-$, 336 amu ($C_{16}H_{32}O_5P$) and 219 amu ($C_7H_8O_6P$) were found.

Empirical formula of cyclipostin F: $C_{23}H_{39}O_7P$, molecular weight: 458.

Example 13

Characterization of cyclipostin P.

Fraction 21, obtained according to Examples 5 and 6, was separated as described in Example 8 and cyclipostin P was isolated by multiple repetition of the chromatographic steps (210 mg) and characterized as in Example 9.

Cyclipostin P was crystallized by dissolving the 210 mg in 3 ml of propan-2-ol and 13 ml of acetonitrile and addition of 8 ml of water. After filtering off and washing with cold acetonitrile, a final yield of 135 mg of cyclipostin was obtained. m.p. 58–59° C.

Retention time: 17.7 minutes.

Appearance: neutral, colorless, waxy substance soluble in oxygen-containing organic solvents, but only slightly soluble in water and petroleum ether.

UV maximum: 228 nm in methanol.

IR bands: 2917, 2852, 1753, 1671, 1471, 1214, 996 and 832 cm$^{-1}$.

By high-resolution FAB mass spectrometry using a nitrobenzylalcohol matrix, the following molecular weight was found: 445.2717 amu, corresponding to (M+H)$^+$ for cyclipostinin P of $C_{23}H_{42}O_6P$. From this, an empirical formula for cyclipostin P of $C_{23}H_{41}O_6P$ resulted, molecular weight: 444.

By electron spray mass spectrometry, in the positive ionization mode (ESI, positive) a peak at 445 amu, corresponding to (M+H)$^+$ was found; moreover, the characteristic peak at 221 amu was found, corresponding to $C_7H_{10}O_6P$. In the ESI negative mode, 443 amu (M–H)$^-$, 321 amu ($C_{16}H_{34}O_4P$) and 219 amu ($C_7H_8O_6P$) were found.

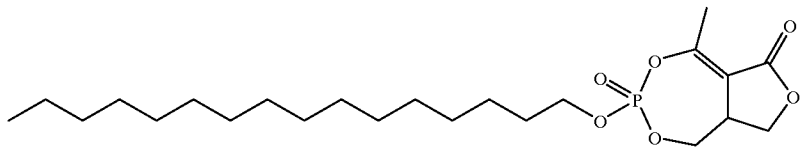

The NMR data for cyclipostin P are shown in Table 2.

TABLE 2

Chemical shifts of cyclipostin P in MeOD at 300 K.

| | $^1$H | $^{13}$C |
|---|---|---|
| 1 | — | 171.08 |
| 2 | — | 114.60 (3.0 Hz)[a] |
| 3 | 3.87 | 40.74 |
| 4 | 4.47/3.85 | 66.05 |
| 5 | 4.30/4.25 | 69.40 (6.0 Hz)[a] |
| 6 | — | 161.47 (8.0 Hz)[a] |
| 7 | 2.40 | 17.90 (4.6 Hz)[a] |
| 1' | 4.24 | 71.62 (6.9 Hz)[a] |
| 2' | 1.73 | 31.16 (6.3 Hz)[a] |
| 3' | 1.41 | 26.38 |
| 4'–13' | 1.34–1.29 | 30.76–30.11 |
| 14' | 1.34–1.29 | 33.07 |
| 15' | 1.31 | 23.72 |
| 16' | 0.89 | 14.42 |

[a] the $^{13}$C/$^{31}$P coupling constants are indicated in parentheses.

Example 14

Characterization of cyclipostin P 2.

Fraction 21, obtained according to Examples 5 and 6, was separated as described in Example 8 and cyclipostin P 2 was isolated by multiple repetition of the chromatographic steps (130 mg) and characterized as in Example 9.

Retention time: 17.1 minutes.

Appearance: neutral, colorless, oily substance soluble in oxygen-containing organic solvents, but only slightly soluble in water and petroleum ether.

UV maximum: 228 nm in methanol.

By high-resolution FAB mass spectrometry using a nitrobenzylalcohol matrix, the following molecular weight was found: 445.2721 amu, corresponding to (M+H)$^+$ for cyclipostin P of $C_{23}H_{42}O_6P$. From this, an empirical formula for cyclipostin P 2 of $C_{23}H_{41}O_6P$ resulted, molecular weight: 444. By electron spray mass spectrometry, in the positive ionization mode (ESI, positive) a peak at 445 amu, corresponding to (M+H)$^+$ was found; moreover the characteristic peak at 221 amu, corresponding to $C_7H_{10}O_6P$, was found. In the ESI negative mode, 443 amu (M–H)$^-$, 321 amu ($C_{16}H_{34}O_4P$) and 219 amu ($C_7H_8O_6P$) were found.

The NMR data for cyclipostin P 2 are shown in Table 3

TABLE 3

Chemical shifts of cyclipostin P 2 in CD$_3$OD at 300 K.

| Position | $^1$H | $^{13}$C |
|---|---|---|
| 1 | — | 171.05 |
| 2 | — | 114.60 (3.2 Hz)[a] |
| 3 | 3.87 | 40.74 |
| 4 | 4.46/3.85 | 66.02 |
| 5 | 4.30/4.25 | 69.38 (6.0 Hz)[a] |
| 6 | — | 161.46 (8.0 Hz)[a] |
| 7 | 2.40 | 17.90 (4.6 Hz)[a] |
| 1' | 4.24 | 71.60 (6.9 Hz)[a] |
| 2' | 1.73 | 31.16 (6.3 Hz)[a] |
| 3' | 1.41 | 26.39 |
| 4'–11' | 1.34–1.29 | 31.04–30.11 |
| 12' | 1.29 | 28.53 |
| 13' | 1.17 | 40.25 |
| 14' | 1.52 | 29.15 |
| 15', 16' | 0.87 | 23.04 |

[a] the $^{13}$C/$^{31}$P coupling constants are indicated in parentheses.

Example 15

Isolation and characterization of cyclipostin N.

Fraction 21, obtained according to Examples 5 and 6, was separated as described in Example 8 and cyclipostin N was isolated by multiple repetition of the chromatographic steps (2 mg) and characterized as in Example 9.

Retention time: 15.9 minutes.

Appearance: neutral, colorless, oily substance soluble in oxygen-containing organic solvents, but only slightly soluble in water and petroleum ether.

UV maximum: 228 nm in methanol.

By high-resolution mass spectrometry under FAB conditions, a quasi-molecular ion (M+H) at 417.2405 was observed corresponding to an empirical formula of $C_{21}H_{38}O_6P$ (theory: 417.2406). Characteristic fragment in the ESI$^+$ mode: 221 amu.

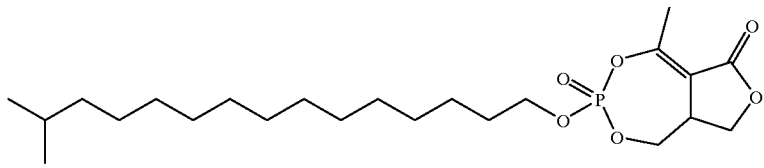

The NMR data for cyclipostin N are shown in Table 4.

TABLE 4

Chemical shifts of cyclipostin N in MeOD at 300 K.

| Position | $^1$H | $^{13}$C |
|---|---|---|
| 1 | — | 171.07 |
| 2 | — | 114.60 (3.1 Hz)[a] |
| 3 | 3.87 | 40.74 |
| 4 | 4.45/3.84 | 66.03 |
| 5 | 4.30/4.25 | 69.39 (5.9 Hz)[a] |
| 6 | — | 161.47 (8.0 Hz)[a] |
| 7 | 2.40 | 17.90 (4.9 Hz)[a] |
| 1' | 4.24 | 71.60 (6.6 Hz)[a] |
| 2' | 1.73 | 31.16 (6.2 Hz)[a] |
| 3' | 1.41 | 26.38 |
| 4'–11' | 1.35–1.26 | 30.76–30.11 |
| 12' | 1.35–1.26 | 33.06 |
| 13' | 1.31 | 23.72 |
| 14' | 0.89 | 14.41 |

[a] the $^{13}$C/$^{31}$P coupling constants are indicated in parentheses.

Example 16

Isolation and characterization of cyclipostin R.

Fraction 21, obtained according to Examples 5 and 6, was separated as described in Example 8 and cyclipostin R was isolated by multiple repetition of the chromatographic steps (8 mg) and characterized as in Example 9.

Retention time: 16.7 minutes.

Appearance: neutral, colorless, crystalline substance soluble in oxygen-containing organic solvents, but only slightly soluble in water and petroleum ether.

UV maximum: 228 nm in methanol.

By high-resolution mass spectrometry under FAB conditions, a quasi-molecular ion (M+H) at 431.2561 was observed corresponding to an empirical formula of $C_{22}H_{40}O_6P$ (theory: 431.2562). Characteristic fragment in the ESI$^+$ mode: 221 amu.

The NMR data for cyclipostin R are shown in Table 5.

TABLE 5

Chemical shifts of cyclipostin R in MeOD at 300 K.

| Position | $^1$H | $^{13}$C |
|---|---|---|
| 1 | — | 171.06 |
| 2 | — | 114.58 (3.2 Hz)[a] |
| 3 | 3.87 | 40.75 |
| 4 | 4.45/3.85 | 66.04 |
| 5 | 4.30/4.25 | 69.40 (6.0 Hz)[a] |
| 6 | — | 161.48 (8.0 Hz)[a] |
| 7 | 2.40 | 17.90 (5.0 Hz)[a] |
| 1' | 4.24 | 71.61 (7.0 Hz)[a] |
| 2' | 1.73 | 31.16 (6.2 Hz)[a] |
| 3' | 1.41 | 26.38 |
| 4'–12' | 1.37–1.25 | 30.74–30.10 |
| 13' | 1.17 | 33.06 |
| 14' | 1.30 | 23.71 |
| 15' | 0.89 | 14.40 |

[a] the $^{13}$C/$^{31}$P coupling constants are indicated in parentheses.

Example 17

Isolation and characterization of cyclipostin R2.

Fraction 21, obtained according to Examples 5 and 6, was separated as described in Example 8 and cyclipostin R2 was isolated by multiple repetition of the chromatographic steps (8 mg) and characterized as in Example 9.

Retention time: 16.4 minutes.

Appearance: neutral, colorless, oily substance soluble in oxygen-containing organic solvents, but only slightly soluble in water and petroleum ether.

UV maximum: 228 nm in methanol.

By high-resolution mass spectrometry under FAB conditions, a quasi-molecular ion (M+H) at 431.2564 was observed corresponding to an empirical formula of $C_{22}H_{40}O_6P$ (theory: 431.2562). Characteristic fragment in the ESI$^+$ mode: 221 amu.

The NMR data for cyclipostin R2 are shown in Table 6.

TABLE 6

Chemical shifts of cyclipostin R2 in MeOD at 300 K.

| Position | $^1$H | $^{13}$C |
|---|---|---|
| 1 | — | 171.06 (1.7 Hz)[a] |
| 2 | — | 114.58 (3.1 Hz)[a] |
| 3 | 3.87 | 40.75 |
| 4 | 4.46/3.85 | 66.03 |
| 5 | 4.30/4.25 | 69.39 (6.0 Hz)[a] |
| 6 | — | 161.47 (8.0 Hz)[a] |
| 7 | 2.40 | 17.90 (4.9 Hz)[a] |
| 1' | 4.24 | 71.60 (6.9 Hz)[a] |
| 2' | 1.73 | 31.16 (6.6 Hz)[a] |
| 3' | 1.41 | 26.38 |
| 4'–10' | 1.37–1.25 | 31.02–30.10 |
| 11' | 1.29 | 28.51 |
| 12' | 1.16 | 40.24 |
| 13' | 1.51 | 29.15 |
| 14', 15' | 0.87 | 23.02 |

[a] the $^{13}$C/$^{31}$P coupling constants are indicated in parentheses.

Example 18

Isolation and characterization of cyclipostin S.

Fraction 21, obtained according to Examples 5 and 6, was separated as described in Example 8 and cyclipostin S was isolated by multiple repetition of the chromatographic steps (0.7 mg) and characterized as in Example 9.

Retention time: 18.5 minutes.

Appearance: neutral, colorless, solid substance soluble in oxygen-containing organic solvents, but only slightly soluble in water and petroleum ether.

UV maximum: 228 nm in methanol.

By high-resolution mass spectrometry under FAB conditions, a quasi-molecular ion (M+H) at 459.2883 was observed corresponding to an empirical formula of $C_{24}H_{44}O_6P$ (theory: 459.2575). Characteristic fragment in the ESI$^+$ mode: 235 amu.

The NMR data for cyclipostin S are shown in Table 7.

TABLE 7

Chemical shifts of cyclipostin S in MeOD at 300 K.

| Position | $^1$H | $^{13}$C |
|---|---|---|
| 1 | — | 170.87 (1.4 Hz)[a] |
| 2 | — | 113.66 (3.1 Hz)[a] |
| 3 | 3.85 | 40.77 |
| 4 | 4.45/3.85 | 66.04 |
| 5 | 4.29/4.24 | 69.17 (6.0 Hz)[a] |
| 6 | — | 165.80 (8.3 Hz)[a] |
| 7 | 2.98/2.82 | 25.05 (4.6 Hz)[a] |
| 8 | 1.16 | 10.86 |
| 1' | 4.25 | 71.57 (6.9 Hz)[a] |
| 2' | 1.74 | 31.19 (6.3 Hz)[a] |

TABLE 7-continued

Chemical shifts of cyclipostin S in MeOD at 300 K.

| Position | ¹H | ¹³C |
|---|---|---|
| 3' | 1.42 | 26.41 |
| 4'–13' | 1.34–1.29 | 30.76–30.11 |
| 14' | 1.34–1.29 | 33.07 |
| 15' | 1.31 | 23.73 |
| 16' | 0.89 | 14.43 | a) the $^{13}C/^{31}P$ coupling constants are indicated in parentheses.

Example 19

Isolation and characterization of cyclipostin T.

Fraction 21, obtained according to Examples 5 and 6, was separated as described in Example 8 and cyclipostin T was isolated by multiple repetition of the chromatographic steps (5 mg) and characterized as in Example 9.

Retention time: 19.1 minutes.

Appearance: neutral, colorless, solid substance soluble in oxygen-containing organic solvents, but only slightly soluble in water and petroleum ether.

UV maximum: 228 nm in methanol.

By high-resolution mass spectrometry under FAB conditions, a quasi-molecular ion (M+H) at 473.3030 was observed corresponding to an empirical formula of $C_{24}H_{46}O_6P$ (theory: 473.3032). Characteristic fragment in the ESI⁺ mode: 249 amu.

The NMR data for cyclipostin T are shown in Table 7.

TABLE 8

Chemical shifts of cyclipostin T in MeOD at 300 K.

| Position | ¹H | ¹³C |
|---|---|---|
| 1 | — | 170.98 (1.7 Hz)ᵃ⁾ |
| 2 | — | 114.39 (3.1 Hz)ᵃ⁾ |
| 3 | 3.87 | 40.78 |
| 4 | 4.46/3.85 | 66.02 |
| 5 | 4.29/4.26 | 69.23 (5.9 Hz)ᵃ⁾ |
| 6 | — | 164.69 (8.7 Hz)ᵃ⁾ |
| 7 | 2.89/2.83 | 33.35 (4.5 Hz)ᵃ⁾ |
| 8 | 1.65 | 20.63 |
| 9 | 0.98 | 13.84 |
| 1' | 4.25 | 71.57 (6.6 Hz)ᵃ⁾ |
| 2' | 1.74 | 31.18 (6.2 Hz)ᵃ⁾ |
| 3' | 1.42 | 26.42 |
| 4'–13' | 1.34–1.29 | 30.78—30.11 |
| 14' | 1.34–1.29 | 33.06 |
| 15' | 1.31 | 23.72 |
| 16' | 0.89 | 14.42 | a) the $^{13}C/^{31}P$ coupling constants are indicated in parentheses.

Example 20

Isolation and characterization of cyclipostin T2.

Fraction 21, obtained according to Examples 5 and 6, was separated as described in Example 8 and cyclipostin T2 was isolated by multiple repetition of the chromato-graphic steps (4 mg) and characterized as in Example 9.

Retention time: 18.7 minutes.

Appearance: neutral, colorless, solid substance soluble in oxygen-containing organic solvents, but only slightly soluble in water and petroleum ether.

UV maximum: 228 nm in methanol.

By high-resolution mass spectrometry under FAB conditions, a quasi-molecular ion (M+H) at 473.3035 was observed corresponding to an empirical formula of $C_{25}H_{46}O_6P$ (theory: 473.3032). Characteristic fragment in the ESI⁺ mode: 249 amu.

The NMR data for cyclipostin T2 are shown in Table 9.

TABLE 9

Chemical shifts of cyclipostin T2 in MeOD at 300 K.

| Position | ¹H | ¹³C |
|---|---|---|
| 1 | — | 170.98 (1.7 Hz)ᵃ⁾ |
| 2 | — | 114.40 (3.1 Hz)ᵃ⁾ |
| 3 | 3.87 | 40.78 |
| 4 | 4.46/3.85 | 66.02 |
| 5 | 4.29/4.25 | 69.23 (5.9 Hz)ᵃ⁾ |
| 6 | — | 164.69 (8.7 Hz)ᵃ⁾ |
| 7 | 2.90/2.83 | 33.35 (4.5 Hz)ᵃ⁾ |
| 8 | 1.65 | 20.63 |
| 9 | 0.98 | 13.84 |
| 1' | 4.24 | 71.57 (6.9 Hz)ᵃ⁾ |
| 2' | 1.74 | 31.18 (6.2 Hz)ᵃ⁾ |
| 3' | 1.42 | 26.42 |
| 4'–11' | 1.37–1.25 | 31.03–30.11 |
| 12' | 1.29 | 28.52 |
| 13' | 1.17 | 40.25 |
| 14' | 1.52 | 29.15 |
| 15', 16' | 0.87 | 23.03 | a) the $^{13}C/^{31}P$ coupling constants are indicated in parentheses.

Example 21

Inhibition of the hormone-sensitive lipase (HSL).

The hormone-sensitive lipase from rats was inhibited in the following concentrations ($IC_{50}$) using trioleoylglycerol as a substrate:

| | |
|---|---|
| Cyclipostin A: | 20 nM, |
| Cyclipostin N: | 450 nM, |
| Cyclipostin P: | 30 nM, |
| Cyclipostin P2: | 40 nM, |
| Cyclipostin R: | 10 nM, |
| Cyclipostin R2: | 220 nM, |
| Cyclipostin S: | 20 nM, |
| Cyclipostin T: | 200 nM, |
| Cyclipostin T2: | 60 nM. |

We claim:
1. A compound of formula I

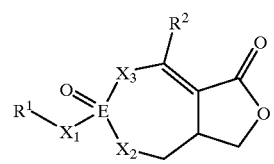

wherein
R¹ is
(a) a carbon chain having 2 to 30 carbon atoms, which can be straight-chain or branched, saturated or unsaturated, carbo- or heterocyclic, and in which the carbon chain is optionally mono- or disubstituted by a radical selected from:
(a)(1) —OH,
(a)(2)=O,
(a)(3) —O—$C_1$–$C_6$-alkyl, in which alkyl is linear or branched, (a)(4) —O—$C_2$–$C_6$-alkenyl, in which alkenyl is linear or branched,
(a)(5) —$C_1$–$C_6$-alkyl, in which alkyl is linear or branched,
(a)(6) -aryl,
(a)(7) —$C_1$–$C_6$-alkylbenzene,
(a)(8) -diphenyl,
(a)(9) —NH—$C_1$–$C_6$-alkyl, in which alkyl is linear or branched,
(a)(10) —NH—$C_2$–$C_6$-alkenyl, in which alkenyl is linear or branched,
(a)(11) —$NH_2$,
(a)(12) =S,
(a)(13) —S—$C_1$–$C_6$-alkyl, in which alkyl is linear or branched,
(a)(14) —S—$C_2$–$C_6$-alkenyl, in which alkenyl is linear or branched, and
(a)(15) halogen,
in which the substituents (a)(1) to (a)(15) are optionally additionally substituted, or
(b)-[-aryl-$(CH_2)_n]_m$, wherein [-aryl-$(CH_2)_n]_m$ is unsubstituted, or mono- or disubstituted by a radical as described in (a)(1) to (a)(15), and n and m independently of one another are integers zero, 1, 2, or 3;

$R^2$ is
$C_1$–$C_6$-alkyl, wherein alkyl is unsubstituted, or mono- or disubstituted by a radical as described in (a)(1) to (a)(15),
$C_2$–$C_6$-alkenyl, wherein alkenyl is unsubstituted or mono- or disubstituted by a radical as described in (a)(1) to (a)(15), or
$C_2$–$C_6$-alkynyl, wherein alkynyl is unsubstituted or mono- or disubstituted by a radical as described in (a)(1) to (a)(15);

E is a phosphorus (P) or sulfur (S) atom; and
$X_1$, $X_2$, and $X_3$ are each selected independently from
—O—,
—NH—,
—N=,
—S—,
—$CH_2$—, and
—$CHR^2$—;

in any stereochemical form, or a mixture of any stereochemical forms in any ratio, or a physiologically tolerable salt or chemical equivalent thereof.

2. A compound as claimed in claim 1, wherein $R^1$ is a carbon chain having 10 to 18 carbon atoms, which can be straight-chain or branched, saturated or unsaturated, carbo- or heterocyclic, wherein the carbon chain is unsubstituted, or mono- or disubstituted by a radical as described in (a)(1) to (a)(15).

3. A compound as claimed in claim 1, wherein $R^1$ is selected from

—$(CH_2)_{15}CH_3$,
—$(CH_2)_{13}CH(CH_3)_2$,
—$(CH_2)_{11}CH(OH)(CH_2)_3CH_3$,
—$(CH_2)_{11}CH(OH)CH_2CH(CH_3)_2$,
—$(CH_2)_{12}CH(OH)(CH_2)_2CH_3$,
—$(CH_2)_{13}CH(OH)CH_2CH_3$,
—$(CH_2)_{14}CH(OH)CH_3$,
—$(CH_2)_{15}CH_2(OH)$,
—$(CH_2)_{16}CH_3$,
—$(CH_2)_{13}C=OCH_2CH_3$,
—$(CH_2)_{12}C=OCH_2CH_2CH_3$,
—$(CH_2)_{11}C=OCH_2CH_2CH_2CH_3$,
—$(CH_2)_{13}CH_3$,
—$(CH_2)_{11}CH(CH_3)_2$,
—$(CH_2)_{14}CH_3$, and
—$(CH_2)_{12}CH(CH_3)_2$.

4. A compound as claimed in claim 1, wherein $R^2$ is $C_1$–$C_6$-alkyl.

5. A compound as claimed in claim 4, wherein $R^2$ is selected from —$CH_3$, —$CH_2CH_3$, and $CH_2CH_2CH_3$.

6. A process for the preparation of a compound as claimed in any one of claims 1 to 5, comprising fermenting the microorganism Streptomyces species HAG 004107, DSM 13381, or one of its variants or mutants under suitable conditions in a culture medium until at least one of said compounds accumulates in the culture medium, isolating said at least one compound from the culture medium, and optionally converting said at least one compound into a chemical equivalent or physiologically tolerable salts thereof.

7. The compound prepared by the process as claimed in claim 6.

8. The process as claimed in claim 6, wherein the fermenting is carried out under aerobic conditions at a temperature between about 18 and 35° C.

9. The process as claimed in claim 6, wherein the fermenting is carried out at a pH between about 6 and 8.

10. A method for inhibiting at least one lipase, comprising administering at least one compound claimed in any one of claims 1 to 5 to a patient in need thereof.

11. A method of treating diabetes, comprising administering at least one compound as claimed in any one of claims 1 to 5 to a patient in need thereof.

12. A pharmaceutical composition, comprising at least one compound as claimed in any one of claims 1 to 5, and a pharmaceutically acceptable carrier.

13. A process for the production of the pharmaceutical composition as claimed in claim 12, comprising bringing the at least one compound into a suitable administration form by adding at least of a suitable excipient or vehicle.

* * * * *